(12) United States Patent
Burge et al.

(10) Patent No.: US 7,247,278 B2
(45) Date of Patent: Jul. 24, 2007

(54) AUTOMATED GROUND WATER MONITORING AND ANALYSIS SYSTEM

(76) Inventors: Scott R. Burge, 6100 S. Maple Ave., #114, Tempe, AZ (US) 85283; Russell W. Burge, 6100 S. Maple Ave., #114, Tempe, AZ (US) 85283; David A. Hoffman, 6100 S. Maple Ave., #114, Tempe, AZ (US) 85283

( * ) Notice: Subject to any disclaimer, the term of this patent is extended or adjusted under 35 U.S.C. 154(b) by 204 days.

(21) Appl. No.: 09/939,934

(22) Filed: Aug. 27, 2001

(65) Prior Publication Data

US 2002/0023479 A1 Feb. 28, 2002

Related U.S. Application Data

(60) Provisional application No. 60/228,312, filed on Aug. 28, 2000.

(51) Int. Cl.
*G01N 30/00* (2006.01)

(52) U.S. Cl. .................. 422/156; 422/99; 422/100; 422/101; 422/68.1

(58) Field of Classification Search ............. 73/864.34, 73/864.35, 864.63; 422/50, 62, 68.1, 100, 422/101; 436/39, 25, 28, 177, 180
See application file for complete search history.

(56) References Cited

U.S. PATENT DOCUMENTS

| 5,033,551 | A | | 7/1991 | Grantom |
| 5,293,934 | A | | 3/1994 | Burge et al. |
| 5,646,863 | A | * | 7/1997 | Morton ...................... 702/23 |
| 5,708,220 | A | | 1/1998 | Burge |
| 6,444,172 | B2 | * | 9/2002 | Fukunaga et al. ......... 422/68.1 |
| 6,491,828 | B1 | * | 12/2002 | Sivavec et al. ............. 210/739 |

* cited by examiner

*Primary Examiner*—Jill Warden
*Assistant Examiner*—Samuel P. Siefke
(74) *Attorney, Agent, or Firm*—Boniard I. Brown (57) ABSTRACT

An automated computer controlled ground water system for monitoring and analysis for an analyte, has a sampling device in a well casing with a valve and sensor to provide a predetermined sample volume, a treatment assembly to prepare a calibration standard, a calibration assembly to provide a standard of known concentration and volume, an analytical assembly to analyze for analyte concentration, and a communication system to receive analysis data and transmit it to a cognizant agency.

16 Claims, 7 Drawing Sheets

AUTOMATED GROUND WATER MONITORING AND ANALYSIS SYSTEM

RELATED APPLICATIONS

Reference is made to our Provisional Application No. 60/228,312, filed Aug. 28, 2000, entitled "Ground-Water Monitoring System".

BACKGROUND AND SUMMARY OF THE INVENTION

1. Field of the Invention

The present invention relates generally to analysis systems for determining the presence and concentrations of hazardous, carcinogenic, etc., chemicals in ground water. In particular, the invention relates to an automated system for operation on site to automatically and independently assay concentrations of analytes of interest, and to communicate analysis data to agencies concerned with health and safety.

2. The Prior Art

Analysis of ground water for analytes of interest has become progressively more important because of concern regarding soil and ground water contamination by industrial chemicals and the like, and by nuclear waste.

The prior art comprises a wide assortment of liquid sampling systems and devices. These fall into three general categories:

(a) devices lowered into a liquid to collect a sample;

(b) devices lowered into a liquid and which pump the liquid to the surface for analysis; and (c) devices lowered into the liquid and which embody self-contained means for analysis of the liquid and the transmitting of analysis data to a processing station.

Among the prior art patents relative to such liquid sampling devices are the following: U.S. Pat. No. 5,293,934 to Burge et al, U.S. Pat. No. 5,033,551 to C. Grantom, and U.S. Pat. No. 5,708,220 to R. Burge.

Liquid sampling devices of the prior art involve certain disadvantages and shortcomings, which it is the purpose of the present invention to overcome.

Devices which obtain samples by lowering a device into the liquid to be sampled, withdrawing the sample from the liquid, and retrieving and collecting samples, involve time-consumption, tedious processes and expense. A primary disadvantage is that contamination of the sample analyzing means within a submersible sampling device necessarily restricts the accuracy of sample analyses which may be performed, expose the instrumentation to risk of damage, unnecessarily increase the cost and complexity of sampling devices, and preclude utilizing such instrumentation for other purposes, as in laboratories.

Devices lifting a column of water equal in height to the distance from the submerged sample collection device to the surface require very high pump outlet pressure, particularly when a sampling device is a substantial distance below ground surface, such as 1,000 ft. or much more.

There has existed substantial and increasing need for an improved water sampling system and method which provides a complete automatic procedure from sampling through analysis, and under computer program control from sampling to disposal of waste samples and communicating the analysis results automatically to provide an assay for use by appropriate agencies.

THE PRESENT INVENTION

The present invention provides an automatic computerized system, apparatus and method for the provision of analyses to identify specific elements and compounds as analytes in a sample automatically provided. The system prepares and standardizes a sample for presentation to an analysis assembly to process a sample by instrumentation to arrive at an assay of the sample. Assay data is sensed and processed for computer print-out and communication via a communication link to inform cognizant agencies. A computer and a control module 120 controls operation and sequencing of the system.

The present ground water monitoring system of the present invention comprises, in a sampling module, a water treatment module, a calibration module, an analytical module, a communication/data logging module, and a waste module. There are embodiments wherein a particular module may not be used, or where the components of two or more modules are combined to form a combination module, which by the operation of this single module can perform the functions of one or more separate modules. The ground water monitoring system may be used without the water treatment module in certain embodiments.

The purpose of the sampling module is to collect ground water samples from a monitoring well. The ground water sample collected within the sampling module may be analyzed within the body of the sampling module or transported to an analytical module located inside or outside of the monitoring well. The water treatment module serves to remove the analyte of interest from the water to be monitored. Alternatively, the water treatment module can be replaced by a reservoir of distilled water or water not containing the analytes of interest. The water treatment module is used to prepare blanks and standards for calibrating a sensor. The advantage of the water treatment module is that it allows water of the same ion strength, temperature, pH and other factors, to be used to calibrate the sensor.

The calibration module calibrates the sensor inside the analytical module. The communication/data logging module transmits or records the data for the user. The waste module may comprise a vessel for containing the waste water, or may include a small treatment unit. The waste treatment unit of the waste module may include cartridges filled with media which will remove specific contaminants or small chambers for removing contaminants, allowing the waste water to be cleaned to concentrations below the concerns of Federal or State regulations.

Primary components of the analytical system are the sample vessel and the sensor therein. The enclosing of the sensor allows for the introduction of samples, standards, and other chemicals such as matrix modifiers. A sensor which is not enclosed inside the sample vessel cannot be interrogated and standardized. The chemical/physical sensor or other device capable of determining the concentration of the analyte in the ground water sample is placed inside this sample vessel. The analytical module may determine the species of interest, either directly in the water sample or by creating a head space over the sample for chemical/physical sensors which respond to the analyte in atmospheres in the head space. The sample vessel has water level sensors which allow predetermined volumes of standards or samples to be introduced into the sample vessel. The presence of two or more water level sensors allows for the dilution of samples or standards and/or adding special solutions to the sample vessel, such as matrix modifiers.

It is feasible to combine the sampling and analytical modules into one unit for sensors fabricated to fit within the confines of a well casing.

The water treatment unit allows for water from the monitoring well either to be introduced directly into the sample chamber or to pass through a media such as activated charcoal to remove the analyte of interest. Other media would include, but not be limited to, ion exchange resins, clays and zeolites. In some instances, the water treatment module may be replaced with a source of analyte free water.

The calibration module may be located in or outside the monitoring well. If the calibration module is within the well, it contains the valving necessary to introduce liquid or gaseous standards to the analytical module. If the calibration module is located outside of the monitoring well, the module contains the valving necessary for the introduction of the samples (from the sampling module) and standards to the analytical module. The calibration standards can be presented to the sensor as a solution (aqueous or other solvent) or a gas. The type of standard depends upon the sensor and the physical attributes of the analyte to be measured, The calibration module allows for introduction of known concentrations of the analyte into the analytical module.

DESCRIPTION OF THE PREFERRED EMBODIMENTS

Figures 1, 2:
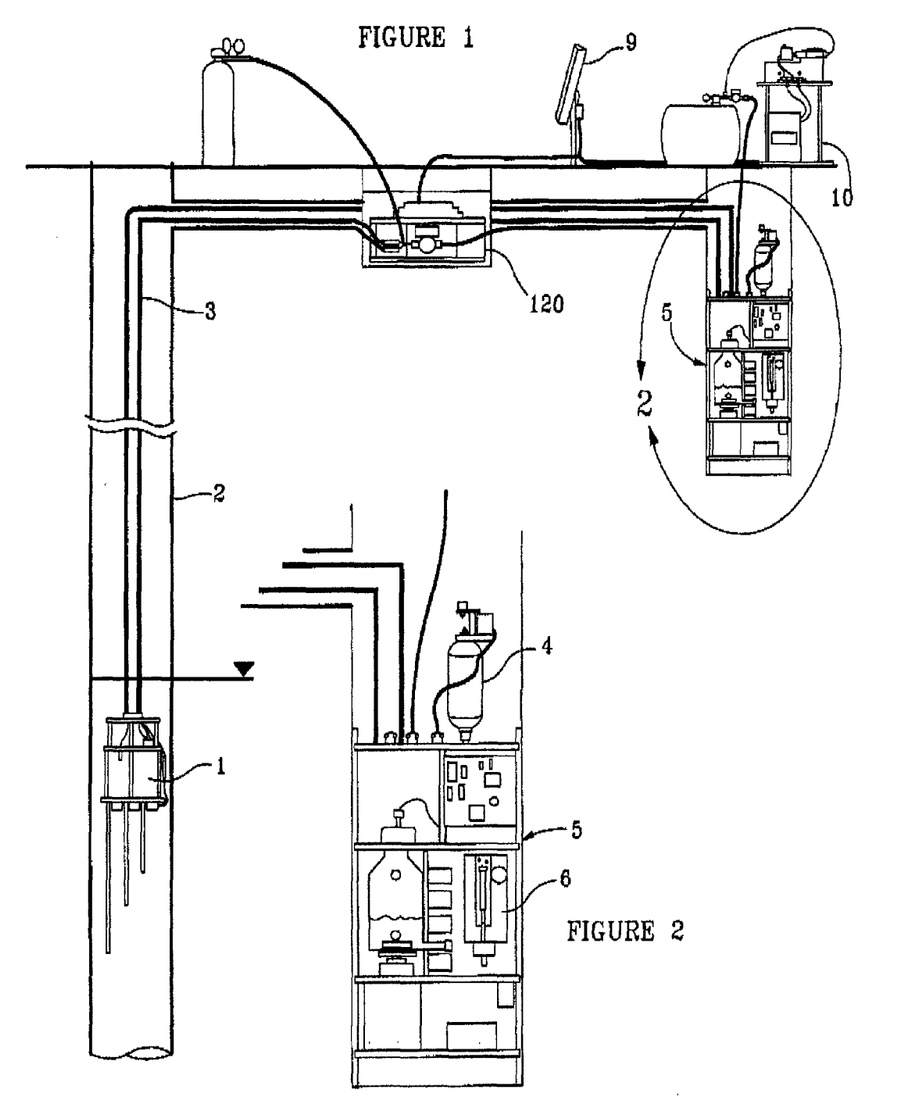
FIG. 1 is a diagrammatic illustration of a preferred embodiment of the present invention.
FIG. 2 is an enlarged view of the portion of FIG. 1 enclosed by circle 2 in FIG. 1.
Figure 3:
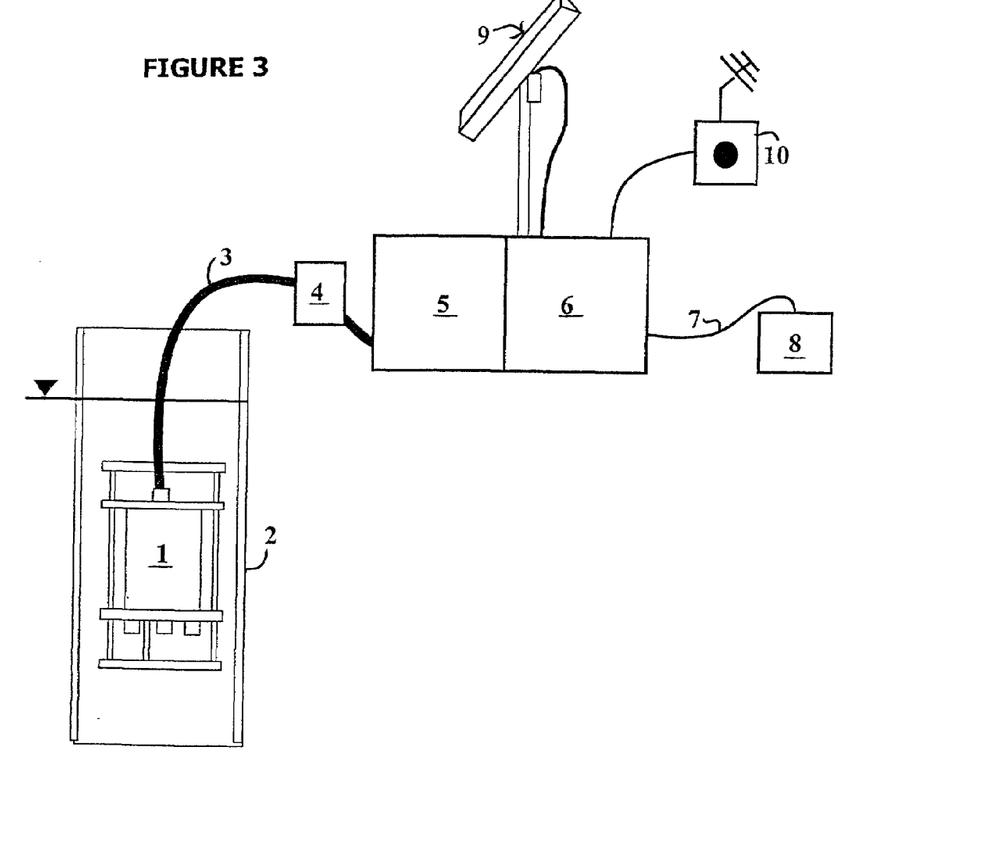
FIG. 3 is a schematic view of an embodiment wherein a sensor is deployed outside of a monitoring well.

Referring to the drawings, FIGS. 1-3 show a basic ground-water monitoring system according to the invention. A sampling module 1 is disposed in a well casing 2 of a well to be monitored. A specimen or sample tube 3 conducts water from the well to a water treatment module 4. The module source of analyte-free water is connected with a calibration module 5 which is attached to an analytical module 6. The waste tube 7 connects the analytical module to a waste reservoir or module 8. A source of electrical power, preferably a solar cell 9, is connected with an analytical module 6. A communication module 10 is connected with the analytical module. Operation of the system and sequencing are controlled by a computer (not herein described) and a control module 120 (FIG. 1).

In the operation of this embodiment, sampling module 1 collects a ground water sample which is transported via tube 3 to water treatment module 4 which is capable of passing the ground-water sample through the module without treatment or conducting the water through a filtering media to remove the analyte of interest. When water not containing the analyte is utilized, it can be supplied from an external source (not shown). The untreated sample passes to analytical module 6. Treated water or analyte-free external water is passed through calibration module 5 for addition of a standard. Alternatively, the standard may be added directly to the sample container from the analytical module. Treated water, with standard added, can be passed to the analytical module for analysis. When the sample standards are analyzed, the sample or standard is transported by waste tube 7 to waste module 8. Data generated by the analytical module by conventional means is relayed to communication module 10, which transmits the data by radio or stores the data.

Figure 4:
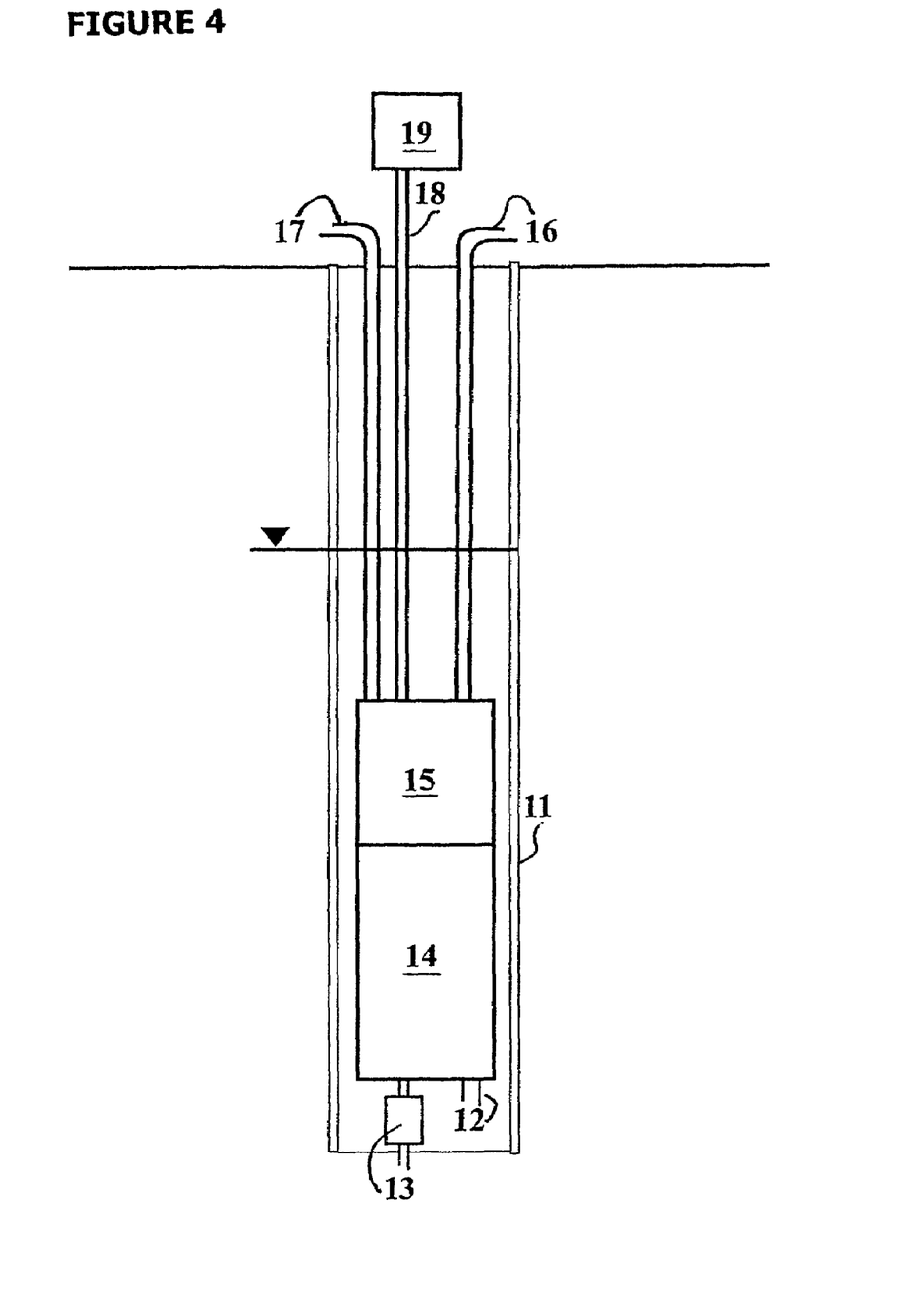
FIG. 4 is an embodiment of the invention wherein the sensor is deployed inside a well.

Referring to FIG. 4, a ground water monitoring system is shown located within the monitoring well casing 11. A sample inlet 12 and water treatment module 13 are attached to the bottom of the sampling/analytical module 14. Alternatively, an external source of analyte free water may be supplied for performing the calibrations. The valving of the calibration module is attached to the sample vessel of the sampling/analytical module 14. A gas line 16 conducts pressurized air, nitrogen or other gases, to the calibration module 15 and/or sampling/analytical module 14. A waste tube 17 is attached to the sampling/analytical module 14. A power/communication cable 18 attaches the communication module 19 to the sampling/analytical module 14.

The operation of the ground water monitoring system located within the well casing as illustrated in FIG. 4 is initiated by the ground water passing through either the sample inlet 12 or the water treatment module 13 into the sampling/analytical module 14. Water conducted through the sample inlet 12 into the sampling/analytical module 14 is analyzed as the sample. After the sample is analyzed, the sample is transported out of the well casing 11, using the waste tube 17, to either a container or treatment unit. The water conducted through the water treatment module, or an external supply of water, is used to prepare the blanks and standards. The water may either be transported through a calibration module 15 for the addition of the standard, or the calibration module 15 adds the standard directly for use in a sampling/analytical module 14. Alternatively, the water treatment module 13 may be deleted and water may be transported from the surface for the preparation of standards and blanks. The data generated from the sampling/analytical module 14 is relayed by the power/communications cable 18 to the communications module 19.

Figure 5:
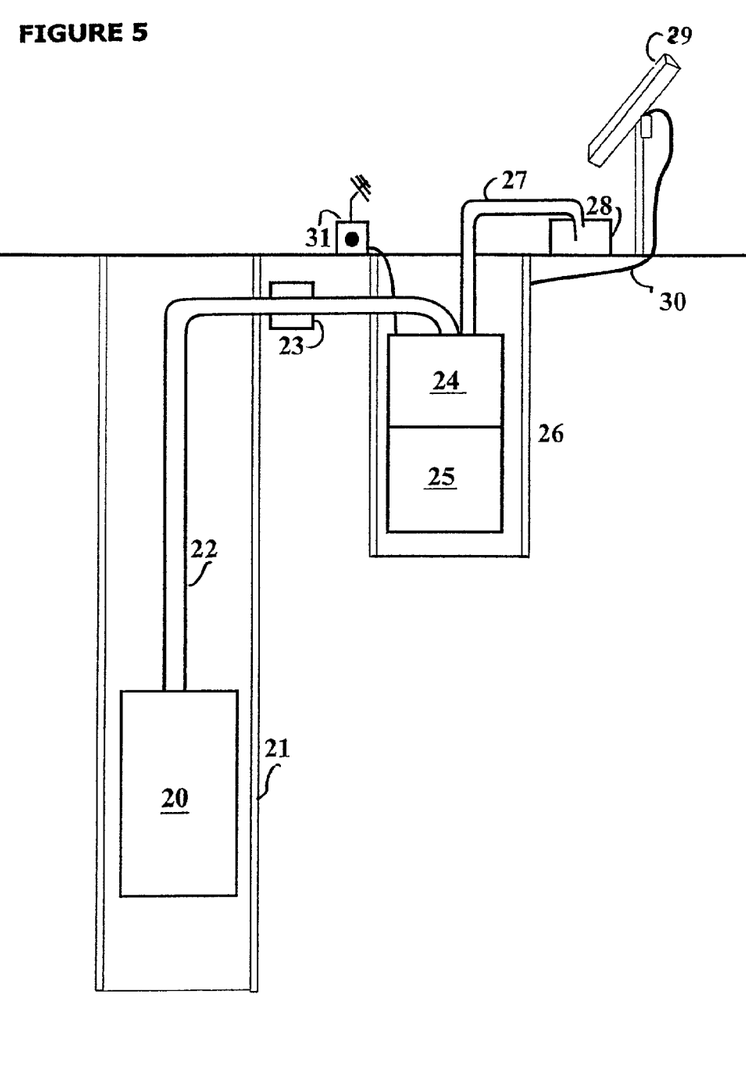
FIG. 5 is a schematic illustration of an embodiment wherein a sensor is deployed in a separate well casing adjacent to a monitoring well for security and environmental control.

Referring to FIG. 5, an embodiment of the ground water monitoring system which disposes the analytical and calibration modules into a separate casing or enclosure adjacent to the monitoring well, is illustrated. The separate casing and enclosure allows for better environmental control, maintenance and security of the ground water monitoring system.

A sampling module 20 is disposed in well casing 21, and a sample tube 22 connects this module with water treatment module 23, which is connected to a calibration module 24 or to a source of analyte-free water (not shown). Calibration module is attached to an analytical module 25. The water treatment module, calibration module and analytical module are disposed in a separate casing 26. Alternatively, a water treatment module may be disposed outside the enclosure or may be replaced by a source of water (not shown) not having the analyte of interest. The waste tube 27 connects analytical module 25 to a waste module 28. Power cable 30 electrically connects the analytical module to a solar cell 29 (or other power source). Communication module 31 is attached to the analytical module 25. Operation of the system of FIG. 5 is similar to that of the system of FIG. 1 except that the modules 24 and 25 are inside a protective casing 26.

Figure 6:
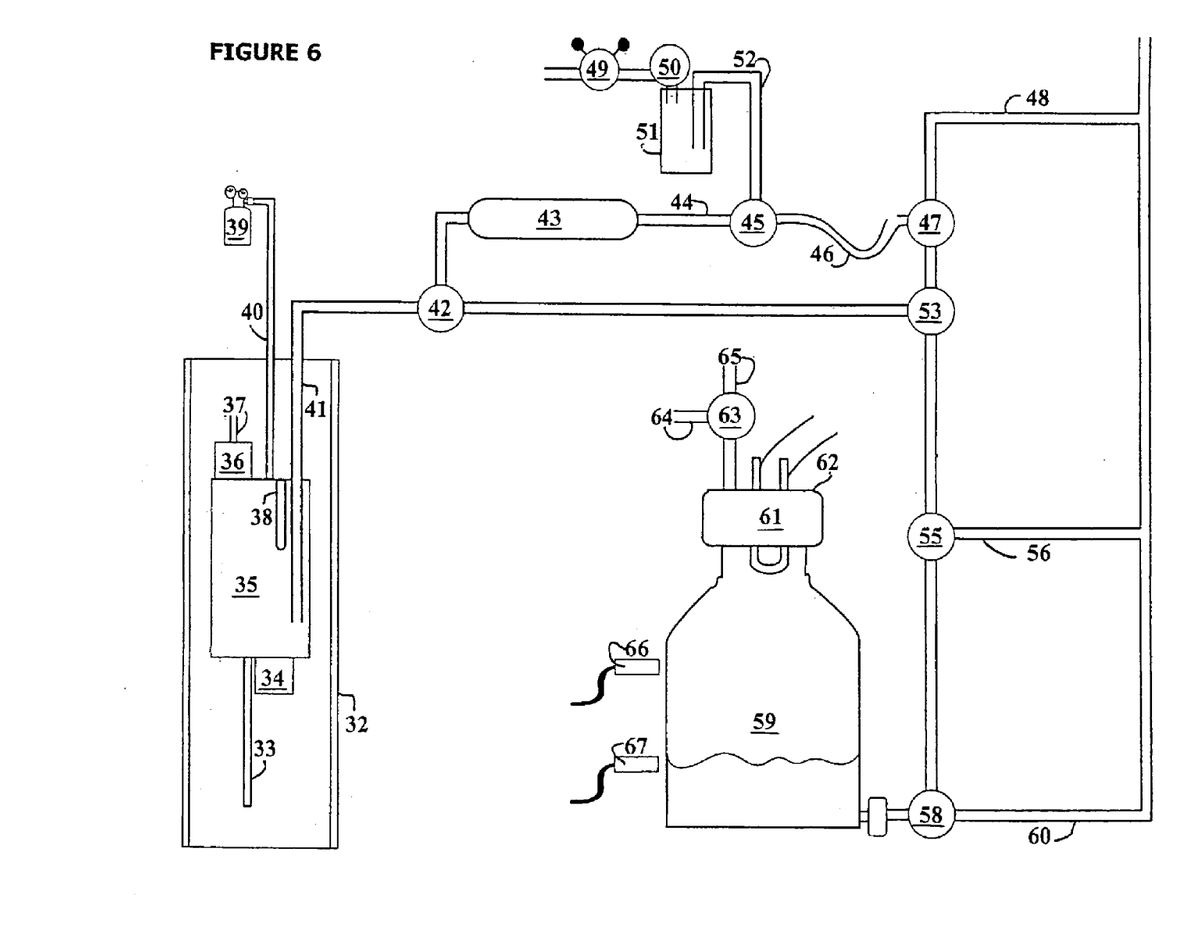
FIG. 6 is a diagrammatic illustration of an embodiment wherein sampling, water treatment, and calibration modules, a sensor vessel, and analytic module for an optrode are deployed in an automated monitoring module.

Referring now to FIG. 6, an example of the sampling module, water treatment module, calibration module and the sensor vessel of the analytical module for an optrode deployed in the automated monitoring system is illustrated.

The sampling module (33-38) is located in the well casing 32, and comprises the several components 33 to 38. Water inlet 33 is attached to sample chamber 35 through water inlet valve 34. A gas valve 36 is connected to the sample chamber 35. A vent tube 37 connects with the gas valve 36. A water sensor 38 is located within the body of the sample chamber 35. A pressurized gas tube 40 connects a source of pressurized gas 39 to a gas valve 36 and the sample chamber 35. A sample tube 41 connects the sample chamber 35 to water treatment valve 42 of the water treatment module 42-44. Alternatively, the sample module 33-38 may be replaced with commercially available pumps. The water treatment valve 42 is connected to the water treatment cartridge 43 and calibration valve 53. The water treatment cartridge 43 is filled with sorbent media for removing and filtering out the analyte of interest. Water treatment cartridge 43 is connected with the standard valve 45 of the calibration module by a water tube 44. Water diverted through treatment cartridge 43 removes the analyte of interest by passing the water through a sorbent media. Water exiting the treatment cartridge 43 is transported to valve 45 of the calibration module via a water tube 44.

The calibration module comprises a source 49 of low pressure gas attached to a valve 50 connected with a bottle 51, which is connected by a tube 52 to the valve 45. This valve is connected to a calibrated loop 46 containing a known volume of standard.

A loop valve 47 is connected to calibrated loop 46 opposite from valve 45. A waste tube 48 is attached to a third port of loop valve 47, as shown. Calibration valve 53 is connected to water treatment valve 42 and loop valve 47. A third port of calibration valve 53 is connected to a diversion valve 55 which is connected to a waste tube 56 and a sample vessel valve 58 which is connected to waste tube 60 and a sample vessel 59 of the analytical module.

In the analytical module, the sample vessel 59 is attached to a sample vessel cap 61 which houses the sensor 62. A port of gas valve 63 is connected to a vent 64 and a pressurized gas tube 65. Water level sensors 66, 67 serve to monitor height of the water column in the sample vessel.

Introduction of the calibration standards is effected by low pressure gas source 49 which gas is conducted by valve 50 to head space of standard bottle 51, which head space is pressurized, transporting the standard through the standard tube 52 into standard valve 45 and calibrated loop 46 into loop valve 47 into the waste tube 48. Thereafter, calibrated loop 46 is filled with a precise volume of standard, which is flushed from calibrated loop 46 by the water from the treatment cartridge 43 via loop valve 47, calibration valve 53, diversion valve 55, sample vessel 58 and into sample vessel 59. Filling of the calibrated loop 46 may be done several times during the filling of sample vessel 59 to create one to several concentrations of standards. Water flows into the sample vessel 59 until water sensor 66, 67 is activated. After analysis of the standard, water in sample vessel 59 is transported through the valve 58 into waste tube 60. Purging of the sample vessel is facilitated by the gas valve 63 which is connected with a source of pressurized gas 65.

The procedure in introducing a sample to the analytical module includes passing the water through water treatment valve 42, calibration valve 53, diversion valve 55, sample valve 58 and sample vessel 59. The filling and emptying of the sample vessel is similar to the filling cycle for the calibration solutions.

Dilution of a sample is accomplished by introducing a sample until lower water level sensor 67 is activated. The remaining water or solution moves through the treatment cartridge 43 or an external source of analyte-free water until upper water level sensor 66 is satisfied. It is thus possible to dilute the sample to allow the sample outside the analytical range of sensor 62 utilized in the ground-water monitoring system.

Operation of this embodiment begins with the water being transported through the water inlet 33 and water inlet valve 34 into the sample chamber 35. Water continues to be conducted into the sample chamber 35 until the water level sensor 38 is satisfied. The gas valve 36 opens the port to the pressurized gas at 39, 40 which pressurizes the head air space in the sample chamber 35. The water is evacuated from the sample chamber 35 by a sample tube 41 and is transported to the water treatment valve 42 of the water treatment module 42-44. Alternatively, this may be replaced with a commercial ground-water pump.

The water treatment valve 42 diverts the ground water through the water treatment cartridge 43 or to the calibration valve 53. Water conducted to the water treatment cartridge 43 is used to prepare the standards. Water transported to the calibration valve 53 is used as the sample. Water diverted through the water treatment cartridge 43 removes the analyte of interest by passing through a sorbent media. Water exiting the water treatment cartridge 43 is transported to the standard valve 45 of the calibration module via a water tube 44.

Figure 7:
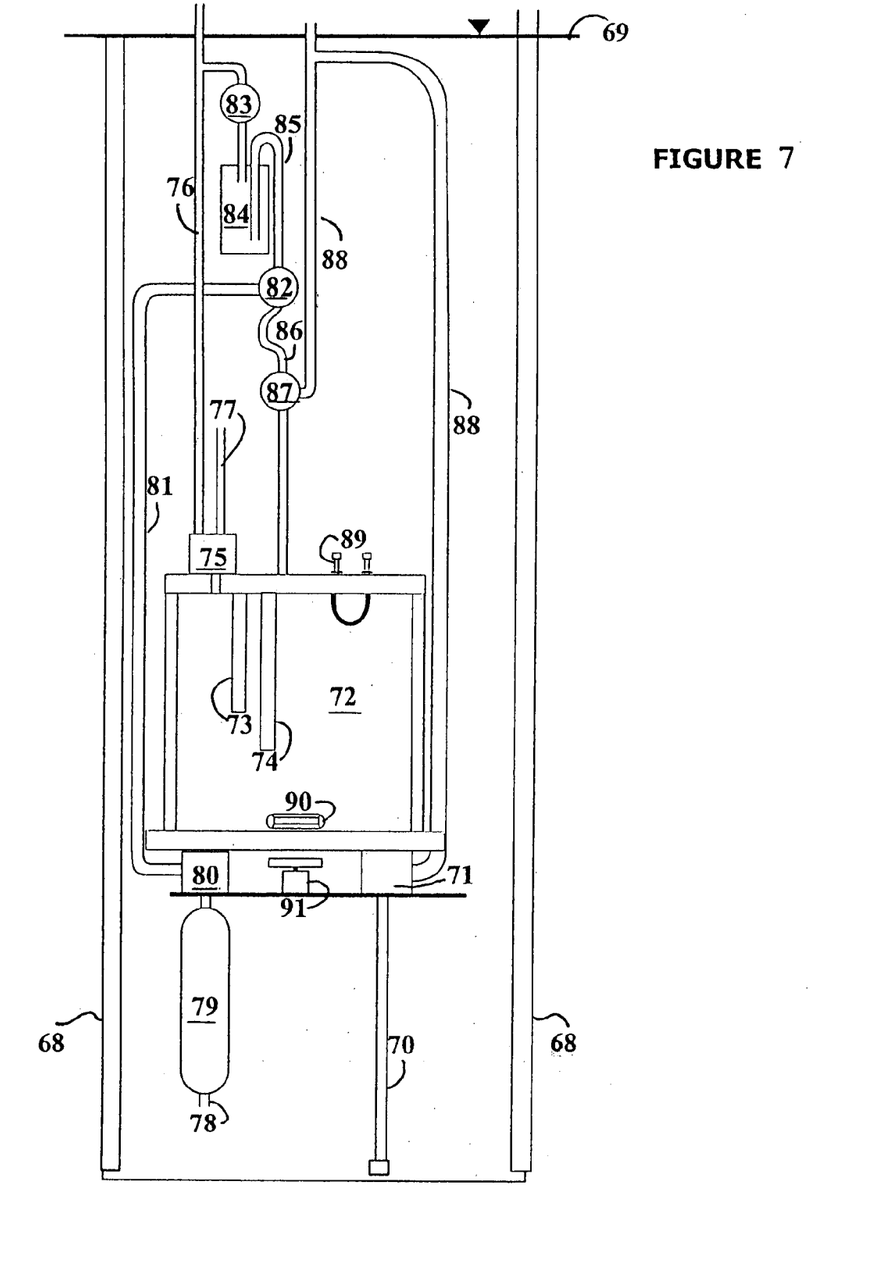
FIG. 7 is a diagrammatic view of an embodiment wherein a sensor is disposed in a monitoring well in a combined sampling and water treatment module.

FIG. 7 shows a sensor deployed in a monitoring well in combination with a sampling/water treatment/calibration analytical module. The analytical/calibration water treatment module is contained within a well casing 68 under the static water level 69. A water inlet 70 is attached to a water inlet valve 71 which is attached to sample chamber 72. A third port (not shown) of inlet valve 71 is connected to a waste tube 88. One or more water level sensors 73, 74 monitor the water level in sample chamber 72. A gas valve 75 is connected with sample chamber 72. The gas valve is connected to a vent 77 and pressurized gas tube 76. A water treatment inlet 78 is connected with water treatment cartridge 79. Water treatment valve 80 is connected atop the treatment cartridge 79, tube 81 and the bottom of chamber 72. Tube 81 is connected to standard valve 82. Gas valve 83 is connected with pressurized gas tube 76 and standard bottle 84. A tube 85 connects standard bottle 84 to standard valve 82. A calibrated loop 86 is attached to valve 82 and loop valve 87 which is connected with waste tube 88 and the top of sample chamber 72. A chemical/physical sensor 89 is disposed in sample chamber 72. A stirring bead 90 is inside sample bottle 72.

If analysis requires sample dilution, lower water sensor 74 controls sample introduction. If dilution is not required, upper sensor 73 terminates sample introduction. These level sensors control the creation and volume of a headspace in the chamber. Certain embodiments (not shown) require no level sensor, and water is introduced into the sample chamber until reaching static water level 69, or by a timer (not shown) connected to stop water introduction into the chamber.

A water sample collected in chamber 72 is analyzed by chemical/physical sensor 89 which may be placed either into the head space above the water sample, or may be inserted into the water. After analysis, a gas valve 75 pressurizes the head space in chamber 72, while water is conducted from inlet valve 71 and via waste tube 88.

If the sensor 89 is to be calibrated with a blank, the water treatment valve 80 is activated, thus to cause ground water to flow via the water treatment inlet 78 and water treatment cartridge 79. Alternatively, a source of analyte-free water may be used. The analyte of interest is removed from the water and the water is passed via water treatment valve 80 into sample chamber 72. The water level rises in the chamber until the water level sensor is activated. In combination with the sample introduction, this allows for dilution of the sample. The water flow into the sample chamber is terminated by the water treatment valve 80 and the analysis initiated. The sample chamber is emptied in a similar method as outlined above.

The operation of the monitoring system with the water treatment/calibration/analytical modules located within a monitoring well is initiated by activating the water inlet valve 71. The hydrostatic pressure causes ground water to fill the sample chamber 72 through the water inlet 70. The water fills the sample chamber until one of the water level sensors 73, 74 de-activates the water inlet valve 71.

If sensor 89 is to be calibrated with a standard containing the analyte of interest, water treatment valve is activated and ground water is passed via water inlet 78, treatment cartridge 79, inlet valve 80 and water tube 81 to standard valve 82. The standard is introduced by activating gas valve 83 to pressurize head space in standard bottle 84 conducting the standard via standard tube 85 to standard valve 82. Standard is then conducted via standard valve 82 through calibrated loop 86 into loop valve 87 and into waste tube 88. Such procedure causes the calibrated loop 86 to be filled with a precise volume of standard. The standard is flushed from loop 86 when the treated water is introduced to standard valve 82, and the treated water transports the standard via loop valve 87 into sample chamber 72. A stirrer motor 91 and stirring bead 90 agitate water in the sample chamber 72.

Figure 8:
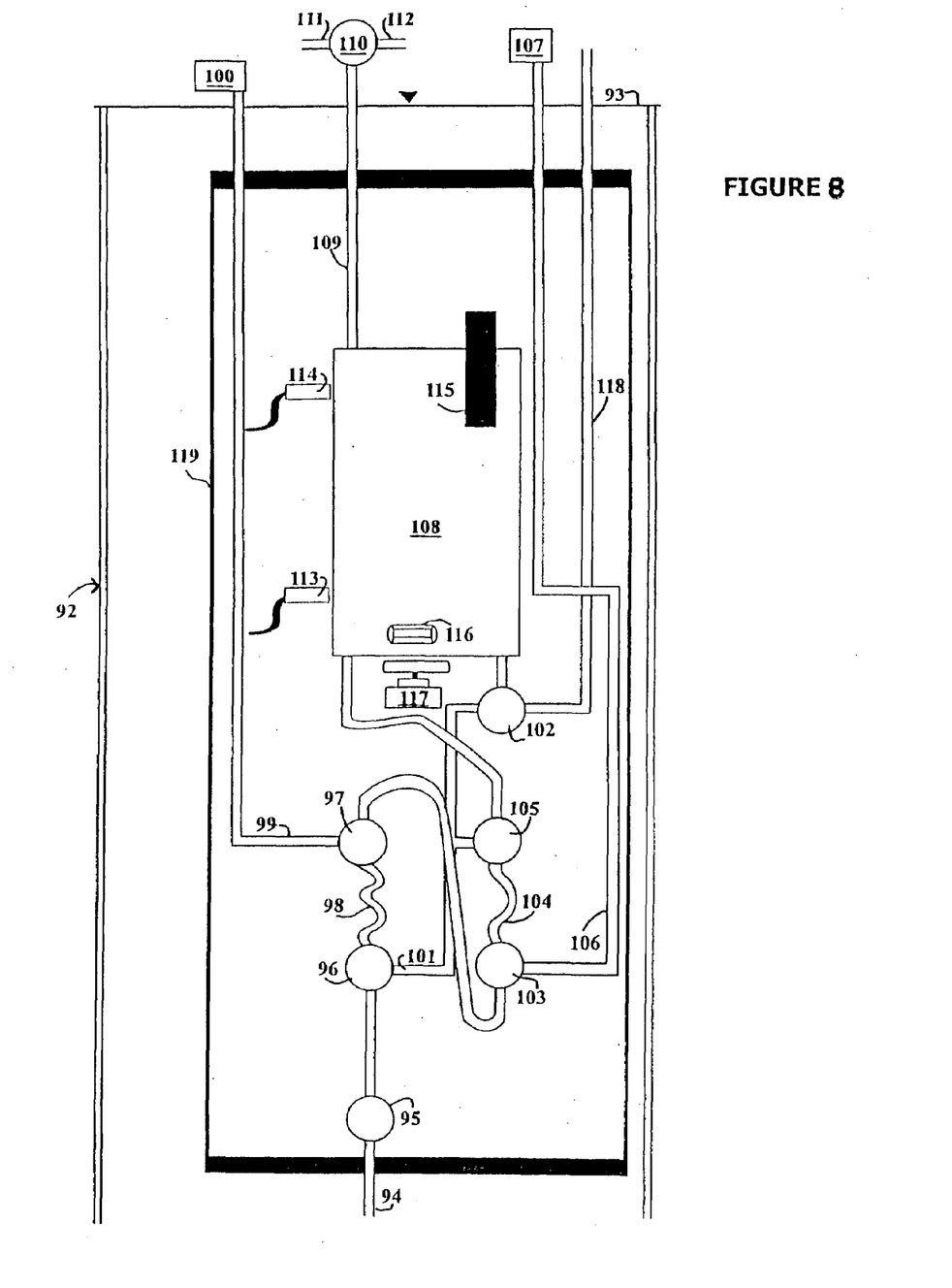
FIG. 8 is a schematic illustration of a monitoring unit utilizing an ion-specific electrode.

FIG. 8 shows an embodiment of the invention wherein a preferred form of electrode which is pH or ion-specific is deployed in a monitoring well, although other types could be utilized, and is located inside a well casing 92 under the static water level 93. A water inlet 94 is connected to an inlet valve 95 connected with matrix modifier loop valve 96. As shown, a calibrated matrix loop 98 connects the matrix modifier loop valve 96. The calibrated matrix loop 98 connects with a third port of the matrix modifier loop valve 96 to the matrix modifier valve 97. The valve 97 is connected to matrix modifier tube 99 which is connected with a matrix modifier reservoir 100 which may be located on the surface of or within well casing 92. As shown, a third port of the matrix modifier valve 97 is connected to the calibration valve 103. A calibration loop 104 is connected with calibration valve 103 with calibration loop valve 105. A third port of the calibration valve 103 is connected to standard tube 106 which is connected with standard reservoir 107 located at the surface or within well casing 92. Calibration valve 105 is connected with a waste tube 101 and the bottom of a sample chamber 108.

The matrix modifier loop 98 and two accompanying valves, matrix modifier valve 97 and matrix modifier loop valve 96, may be disposed after admission of calibration loop 104, calibration valve 103 and calibration loop valve 105. The location of the matrix introduction, relative to standard introduction, is not important to the operation of the device. The top of sample chamber 108 is connected with a gas vent tube 109 connected to a valve 110 disposed above or below static water level 93 in casing 92. An air tube 111 and vent tube 112 are connected to the gas vent valve 110.

An electrode 115 is connected with the interior of chamber 108, and a stirring head 116 is disposed in the chamber, and a stirring motor 117 mounted beneath the chamber, as shown.

A protective casing 119 encloses the entire assembly under static water level 93, as shown in FIG. 8. One or more water level sensors 113, 114 may be disposed inside or outside of the sample chamber. Operation of the system of the invention allows a pH, ion-specific other type electrode to be deployed in a monitor well, requiring a water inlet valve 95 to be activated to cause water to pass through inlet 94, and water flows into the device because of head pressure between inlet 94 and static water level 93.

The ground-water sample passes via inlet valve 95 and matrix modifier loop valve 96, and is then conducted via the matrix modifier loop 98, matrix modifier valve 97, calibration water valve 103, calibration loop 104, calibration loop valve 105 and into sample chamber 108.

Addition of the matrix modifier may be accomplished using one of two methods now described. The amount of matrix modifier may be measured by modifier loop 98. The procedure to add the matrix modifier is by activating matrix modifier loop 96 and matrix modifier valve 97, thus causing matrix modifier solution in the matrix modifier reservoir 100 to pass via tube 99, matrix modifier valve 97, matrix modifier loop 98, modifier loop valve 96, and into waste tube 101. After a short time, the program deactivates the matrix modifier loop 96 and matrix modifier valve 97, thus causing an exact amount of matrix modifier solution to be contained in the matrix modifier loop 98 which is flushed into the sample chamber 108 by opening inlet valve 95, modifier loop valve 96, matrix modifier loop 98, matrix modifier valve 97, calibration valve 103, calibration loop 104, calibration loop valve 105, and into the sample chamber 108.

The second method of producing the matrix modifier is to remove matrix modifier valve 96 and matrix modifier loop 98, and allow the matrix modifier to be introduced via matrix modifier valve 97, calibration valve 103, calibration loop 104, calibration loop valve 105 and into sample chamber 108. The solution will rise into the sample chamber 108 until the lower water level sensor 113 or upper water level sensor 114 is activated. The procedure allows for a precise volume of matrix modifier to be introduced in the chamber 108.

To calibrate electrode 115, calibration valve 103 and loop valve 105 are activated to pass the standard to the standard reservoir 107 via standard tube 106, calibration valve 103, calibration loop 104 and loop valve 105 to waste tube 101. After a time, calibration valve 103 and calibration loop valve 105 will be activated, thus causing an exact amount of standard solution to be contained in the calibration loop 104, which is flushed into the sample chamber by opening inlet valve 94, matrix modifier loop 96, matrix modifier loop 98, matrix modifier valve 97, calibration valve 103, calibration loop 104, calibration loop valve 105 and into sample chamber 108. In one embodiment of the invention (earlier described), no matrix modifier loop valve and no matrix modifier loop are utilized.

During the foregoing operation, gas vent valve 110 vents the head space in chamber 108 to atmosphere. The filling operation is halted when the water level in the chamber rises inside the gas/vent tube 109 to the static water level 93, thus to initiate the analytic phase of operation. Stirring motor 117 is activated to agitate the sample in the chamber with the stirring bead 116. Electrode 115 measures the concentration of the analyte of interest in either a sample or in a standard.

Upon completion of an analysis, gas/vent valve 110 is activated to allow a source of compressed gas to pressurize the head space of the sample chamber and simultaneously, waste valve 102 is activated to drain the sample chamber via waste valve 102 and waste tube 118.

It will be understood that various changes and modifications may be made from the preferred embodiments discussed above without departing from the scope of the present invention, which is established by the following claims and equivalents thereof.

The inventors claim:

1. An automated computer-controlled field-deployable monitoring instrument system for collection and analysis of environmental contaminants and determining the concentration of an analyte of interest in ground water, industrial and surface water, comprising:
    diversion means dividing a water sample into first and second flow paths, said first flow path directing the water sample to a sample vessel for analysis, and the second flow path passing the water through a water treatment cartridge containing a sorbent media to eliminate the analyte of interest before introduction of water into the sample vessel,
    means to calibrate said instrument,
    a calibration assembly to add a standard of predetermined concentration of analyte to the water after it passes through a water treatment cartridge containing a sorbent media to eliminate the analyte of interest,
    a sample vessel to receive water from said single flow path to determine the concentration of the analyte in the sample water for either of the first or second flow paths, and
    means between the calibration assembly and the sample vessel to reunite said first and second flow paths into a single flow path.

2. An automated monitoring system according to claim 1, and further comprising a calibration loop for establishing a predetermined amount of standard solution.

3. An automated monitoring system according to claim 1, and further comprising:
    means to provide a matrix modifier, and
    a valved loop defining a volume of matrix modifier introduced into the sample chamber.

4. An automated monitoring system according to claim 1, and further comprising a casing for the analytical and calibration assemblies to provide improved environmental control, ease of maintenance and security.

5. An automated monitoring system according to claim 1, and further comprising means for stirring a ground water sample to enhance volatization of concentration of the analyte in the sample.

6. An automatic monitoring system according to claim 1, wherein trichloroethylene is the analyte of interest, and monitoring and analysis are performed utilizing an optrode assembly and procedure.

7. A method for determining concentration of an analyte of interest in ground water and surface water, comprising:
    providing a field deployable automated computer-controlled monitoring system and instrument for determining concentration of an analyte of interest in ground water and surface water,
    calibrating said instrument,
    collecting and transporting a water sample to a preparatory treatment assembly,
    passing the water sample to diversion means to divide the water sample into first and second flow paths, said first flow path directing the water sample to a sample vessel for analysis, and the second flow path passing the water through a water treatment cartridge containing a sorbent media to eliminate the analyte of interest before introduction of water into the sample vessel,
    passing the water sample to a calibration assembly to add a standard of predetermined concentration of analyte to the water sample after it passes through a water treatment cartridge containing a sorbent media to eliminate the analyte of interest,
    reuniting said first and second flow paths into a single flow path, and
    passing the single flow water sample to an analytical assembly to determine the concentration of the analyte in the sample water for either of the first or second flow paths.

8. A method according to claim 7, and further comprising:
    introducing calibration standards into a standard container and transporting the standard by a sample vessel.

9. A method according to claim 7, and further comprising the steps of:
    said calibration of the instrument is accomplished by providing a predetermined amount of standard solution via a calibration loop and passing it into the sample chamber.

10. A method according to claim 9, and further comprising:
    passing the sample from a well casing to a calibration system to prepare blanks or standards for addition of the standard directly for use in the analytical assembly.

11. A method according to claim 7, and further comprising the steps of:
    introducing the sample into a sample vessel until a lower sensor is satisfied, and
    adding water to the sample vessel from a water treatment cartridge until an upper water level sensor in the sample vessel is satisfied to provide a predetermined dilution.

12. A method according to claim 7, wherein the analyte of interest is trichloroethylene and analysis utilizes an optroduce assembly.

13. A method according to claim 7, and further comprising relaying analysis data from the analytical assembly to a communication system for transmission to a cognizant agency.

14. An automated monitoring system according to claim 1, and further comprising a sampling device within a well casing and comprising valve means and water level sensor means to provide a ground water sample of predetermined volume.

15. An automated monitoring system according to claim 14, and further including a treatment assembly to receive the sample from the sampling device, said treatment assembly comprising means to provide a calibration standard for the analytical assembly, and one of (a) a treatment cartridge to filter the sample and a calibration sensor, (b) a source of analyte-free water connected with the treatment assembly.

16. An automated monitoring system according to claim 1, and further comprising means to receive analysis and assay data from the analytical assembly to transmit the data to a cognizant agency.

* * * * *